United States Patent
McLorg

(10) Patent No.: US 11,350,936 B1
(45) Date of Patent: Jun. 7, 2022

(54) SPRING SUTURE FOR PRIMARY CLOSURE OF SURGICAL INCISIONS

(71) Applicant: Anthony Barr McLorg, Gates Mills, OH (US)

(72) Inventor: Anthony Barr McLorg, Gates Mills, OH (US)

(73) Assignee: Anthony Barr McLorg, Gates Mill, OH (US)

( * ) Notice: Subject to any disclaimer, the term of this patent is extended or adjusted under 35 U.S.C. 154(b) by 618 days.

(21) Appl. No.: 15/714,196

(22) Filed: Sep. 25, 2017

Related U.S. Application Data

(63) Continuation of application No. 14/271,387, filed on May 6, 2014, now abandoned.

(60) Provisional application No. 61/821,334, filed on May 9, 2013.

(51) Int. Cl.
*A61B 17/08* (2006.01)

(52) U.S. Cl.
CPC ...... *A61B 17/085* (2013.01); *A61B 2017/081* (2013.01)

(58) Field of Classification Search
CPC ............ A61B 17/085; A61B 2017/081; A61B 2017/086; A61B 17/08
See application file for complete search history.

(56) References Cited

U.S. PATENT DOCUMENTS

| | | | | |
|---|---|---|---|---|
| 2,371,978 A * | 3/1945 | Perham | ................ | A61B 17/085 606/216 |
| 3,789,851 A * | 2/1974 | LeVeen | .............. | A61B 17/0466 606/148 |
| 4,702,251 A * | 10/1987 | Sheehan | .............. | A61B 17/085 606/216 |
| 4,815,468 A * | 3/1989 | Annand | ............... | A61B 17/085 606/216 |
| 5,047,047 A * | 9/1991 | Yoon | .................... | A61B 17/083 606/213 |
| 2007/0293888 A1* | 12/2007 | Harren | ............... | A61B 17/0057 606/201 |
| 2008/0146982 A1* | 6/2008 | Rastegar | .............. | A61B 17/085 602/43 |
| 2009/0240186 A1* | 9/2009 | Fang | .................... | A61B 17/085 602/54 |
| 2011/0106026 A1* | 5/2011 | Wu | ..................... | A61M 1/0088 604/319 |

(Continued)

*Primary Examiner* — Jing Rui Ou
(74) *Attorney, Agent, or Firm* — C. Brandon Browning; Maynard, Cooper & Gale, PC

(57) ABSTRACT

A spring suture for primary closure of surgical incisions includes a center spring hingedly connected at each end with surgical tape. In one embodiment, the tape is connected to the center spring through a tape clamp and pin hinge. In another embodiment, the tape is connected to the center spring through welding flanges attached to membrane hinges. In operation, when the spring suture is in place on a wound or incision line, the distal ends of the surgical tape relative to the center spring, in conjunction with the center spring, are adapted to produce closure forces along the incision line that are remote from the incision, enabling such forces to act through the thickness of the skin through shear force transfer and provide closure force at the dermal level of the skin that is initially applied at the epidermal level, thus overcoming the problem of skin inversion at incision line common to skin tapes of the prior art.

13 Claims, 6 Drawing Sheets

(56) References Cited

U.S. PATENT DOCUMENTS

2012/0221044 A1\* 8/2012 Archibald .............. A61B 17/08
   606/214
2014/0128819 A1\* 5/2014 Eaves .................. A61B 17/085
   604/264

\* cited by examiner

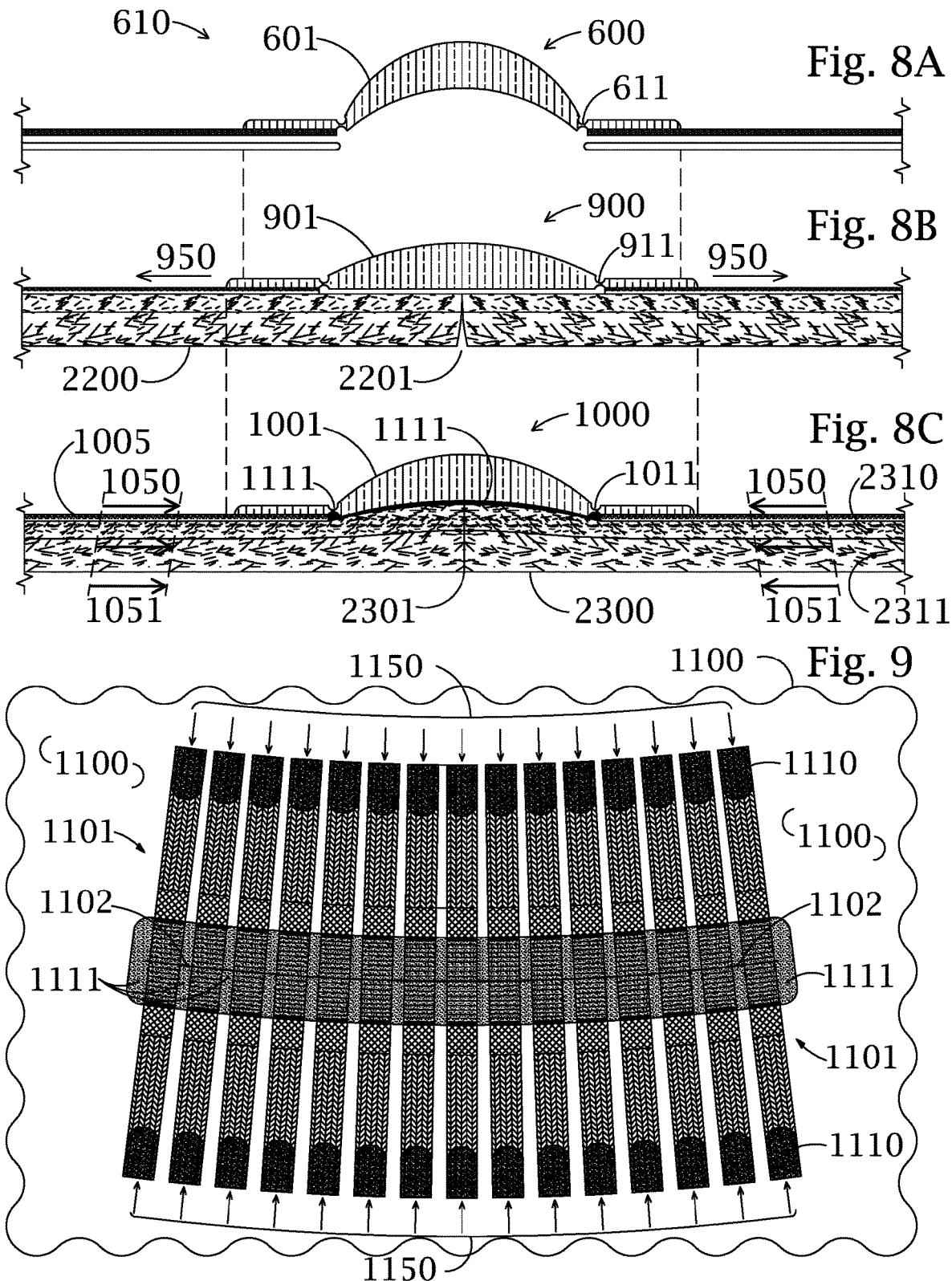

US 11,350,936 B1

SPRING SUTURE FOR PRIMARY CLOSURE OF SURGICAL INCISIONS

CROSS REFERENCE TO RELATED APPLICATIONS

This application claims the benefit of and incorporates by reference co-pending U.S. Non-provisional patent application Ser. No. 14/271,387, filed May 6, 2014, which claims priority to U.S. Patent Application Ser. No. 61/821,334, filed May 9, 2013.

SUMMARY OF THE INVENTION

The present invention is directed to a suture including an elongate resilient spring member having a first end, a second end, a midsection, a convex outer face, an inner face opposing the outer face, a variable thickness extending to and between the inner face and the outer face that progressively decreases moving bilaterally from the midsection toward the first end and the second end, and a bilateral, tapered cross-section. A first attachment strip is coupled to the first end and a second attachment strip is coupled to the second end, the first and second attachment strips being configured for adhering to a wearer. The spring member is movable between a non-stressed state and a stressed state. When in the non-stressed state, the inner face is concave-shaped, and when in the stressed state, the inner face is essentially flat.

In one embodiment, first attachment strip is connected to the spring member through an attachment member and a hinge member disposed on the first end. In another embodiment, a membrane hinge defines the hinge member and welding flange defines the attachment member. In yet another embodiment, the welding flange, the hinge member and the spring member comprise a single, continuous extrusion.

The present invention is further directed to a suture including a spring member including a first end portion, a second end portion, a length extending between the first end portion and the second end portion and having a midsection, a convex outer face defining a first radius, an inner face opposing the outer face, a thickness extending to and between the convex outer surface and the inner surface that progressively decreases moving bilaterally from the midsection towards the first end portion and the second end portion. A first attachment strip coupled to the first end portion, and a second attachment strip is coupled to the second end portion. The spring member is configurable between a non-stressed state wherein the inner face is concave-shaped, and a stressed state. When the suture is in the stressed state, the convex outer face defines a second radius that is greater than the first radius. When the suture is in the stressed state, the inner face is essentially flat.

The present invention is also directed to a suture including an elongate resilient member including a first end portion, a second end portion opposing the first end portion, a midsection, an outer face configured to face away from a wearer, an inner face configured to face towards the wearer and tapered cross-section. A first attachment strip coupled to the first end portion, and a second attachment strip coupled to the second end portion. When the resilient member is a non-stressed state, the inner face is concave-shaped and the outer face is convex-shaped and defines a first radius. When the resilient member is in a stressed state, the inner face is essentially flat and the outer face defines a second radius that is greater than the first radius.

BRIEF DESCRIPTION OF THE DRAWINGS

FIG. 8A is a partial side elevational view of a cross section of an enlarged central section of a suture, built in accordance with a membrane hinge embodiment of the present invention, in a non-stressed state, prior to being attached to a wearer.

FIG. 8B is a partial side elevational view of a cross section of an enlarged central section of a suture, built in accordance with a membrane hinge embodiment of the present invention, with both end sections attached to a wearer and with a pre-stressed spring prior to retraction of the spring.

FIG. 8C is a side elevational view of a cross section of an enlarged central section of a suture, built in accordance with a membrane hinge embodiment of the present invention, in a retracted state and with both end sections attached to a wearer.

FIG. 9 is a top plan view of a plurality of sutures applied to a wearer, in an arc pattern, for closure and treatment of a large incision.

DETAILED DESCRIPTION OF THE INVENTION

The present invention is directed to a suture including a curved center spring configured for imparting a desired magnitude of closure force across an incision. The curved center spring is defined by an outer convex face, an opposing inner face and a variable thickness extending to and between the outer face and the inner face. The variable thickness of the spring is greatest at the center of the spring and progressively decreases moving laterally therefrom so that the spring exhibits a bilateral, tapered cross-section. The center spring is configurable between a non-stressed state, where the inner face is concave-shaped and the outer convex face defines a first radius, and a stressed state, where the convex outer face defines a second radius that is greater than the first radius and the inner face is essentially flat.

Figure 1A:
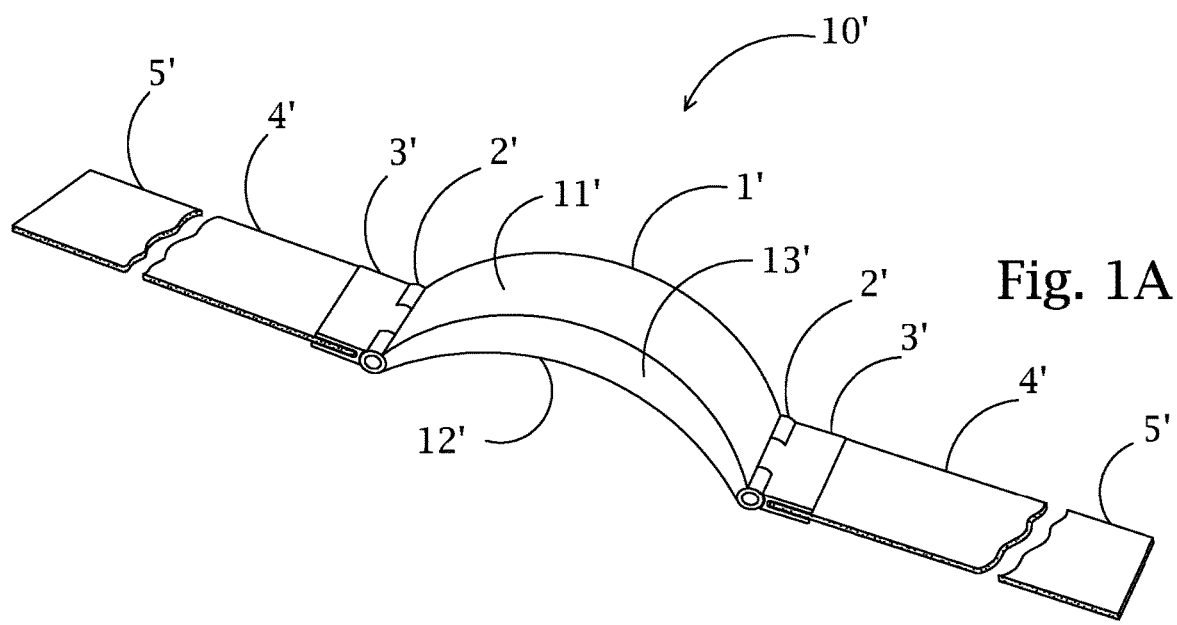
FIG. 1A is a side perspective view of a suture built in accordance with a pin hinge embodiment of the present invention and with a partial sectional view of its surgical tape.

Referring now to the drawings and in particular FIG. 1A, a pin hinge suture 10' for primary closure of surgical incisions is shown having a center spring 1', with an outer face 11', an inner face 12' and a variable thickness 13' extending therebetween, hingedly attached through pin hinge 2' at each end to a tape clamp 3' attached to surgical tape 4', together with distal end 5'. When mechanically stretched apart, spring 1' stores energy from being stretched and uses the energy to exert an opposing compression force. In this regard, the center spring 1' provides a resilient means for storing and releasing mechanical energy. In this embodiment, a pin hinge 2' defines each hinge member. By such a mechanism, when the center spring 1' of the suture 10' is stretched from its non-stressed form, i.e., inner and outer faces 12', 11' of spring 1' exhibiting respective concave and convex shapes, to a stressed, flattened form, i.e., inner face 12' is essentially flattened and the radius of the curve defined by outer face 11' is increased, through the application of manual force, the center spring 1' automatically exerts a specific compression force biasing the center spring 1' to return to its original form.

Tape clamps 3' are attached to pin hinges 2' at each end of the center spring 1' and serve to fasten the center spring 1' to the surgical tape 4', 5'. The surgical tape 4', 5' is embodied as conventional surgical tape and provides an attachment means that is connected to the center spring 1' for supplying energy to the center spring 1' and transferring energy released from center spring 1' to skin. The surgical tape 4', 5' is shown as having a proximal surgical tape end 4' and a distal surgical tape end 5'. When the suture 10' is in place on a wound or incision line, the distal surgical tape ends 5', in conjunction with the center spring 1', produce closure forces along the wound or incision line that are remote from the incision, enabling such forces to act by shear force transfer, through the thickness of the skin to provide closure force at the dermal level of the skin that is initially applied at the epidermal level.

Figure 1B:
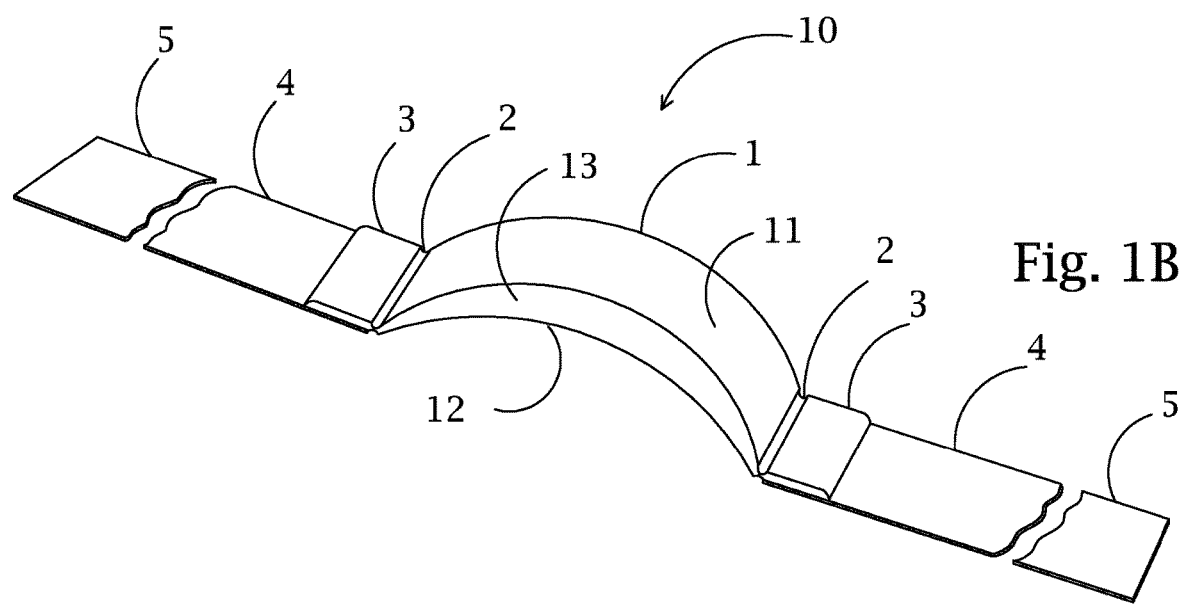
FIG. 1B is a side perspective view of suture built in accordance with a membrane hinge embodiment of the present invention and with a partial sectional view of its surgical tape.

Referring now to FIG. 1B, a membrane hinge suture 10 for primary closure of surgical incisions is shown having a center spring 1 hingedly attached at each end to a welding flange 3 through a membrane hinge member 2, with surgical tape 4, 5 extending from each welding flange 3. In contrast to the pin hinge suture embodiment, in the membrane hinge suture 10 membrane hinges 2 define the hinge members, supplying a hinge joint on either side of the center spring 1 as well as welding flanges 3 to enable the attachment of surgical tape 4, 5. Together, each membrane hinge 2 and welding flange 3 assembly defines a connecting means for hingedly attaching the tape 4 and 5 to the spring 1. Both proximal ends of the surgical tape 4 are attached to the welding flanges 3 through thermal bonding. It is contemplated, however, that other permanent attachment mechanisms, such as a discrete adhesive, may be employed.

In the preferred version of this embodiment, the center spring 1, membrane hinges 2 and the welding flanges 3 are defined as a continuous extrusion that is attached to the surgical tape 4, 5. Such a construction enables the manufacture of an entire sheet of a spring assembly, which is then slit to make the individual suture strips, or alternately as a continuous line process.

Despite any structural variations, however, the mechanical action of the spring suture, whether embodied with a pin hinge or a membrane hinge, is essentially similar to that of the center spring acting through the distal ends of two opposing surgical tapes for the provision of dermal level closure forces.

Figure 2A:
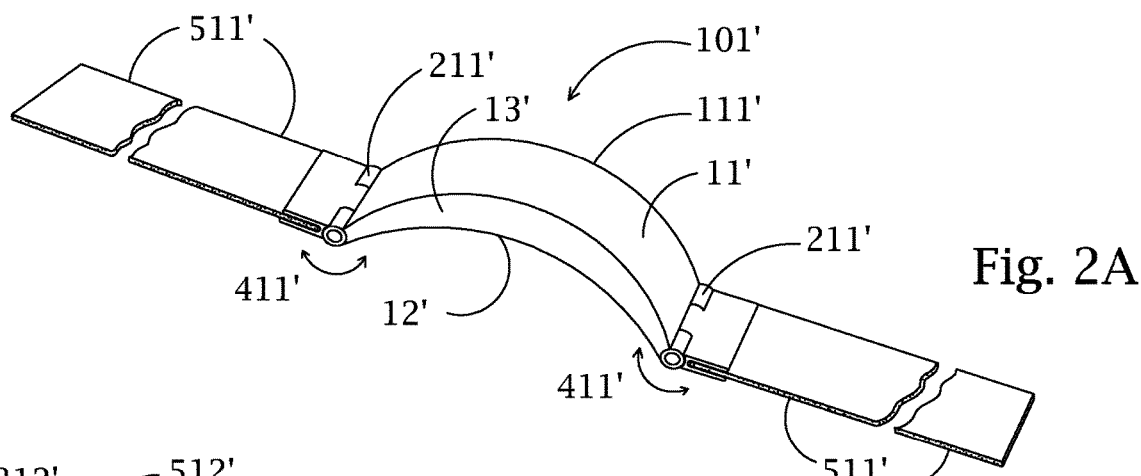
FIG. 2A is a side perspective view of a suture, built in accordance with a pin hinge embodiment of the present invention, with its spring in a non-stressed state and a partial sectional view of its surgical tape.
Figure 3A:
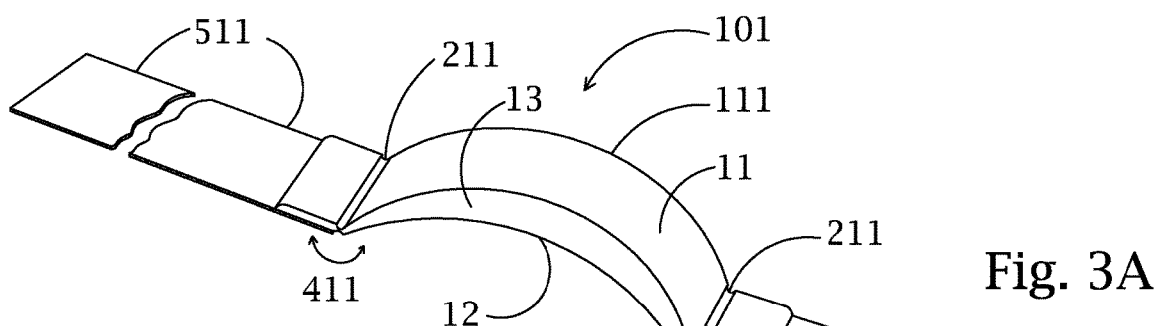
FIG. 3A is a side perspective view of a suture, built in accordance with a membrane hinge embodiment of the present invention, with its spring in a non-stressed state and a partial sectional view of its surgical tape.

Referring now to FIGS. 2A and 3A, embodiments of the spring suture 101', 101 are shown in the non-stressed state of operation. The non-stressed state defines the spring suture 101', 101 as it would be manufactured, once the packaging and tape release strips (not shown here) have been removed, or otherwise when it is not in use. In the non-stressed state, the center spring 111', 111 maintains its resting, convex-concave form having a convex outer face 11' and a concave inner face 12', with the hinge members 211', 211 enabling movement in one plane, of the surgical tape 511', 511 relative to the center spring 111', 111 by the action of vertical swinging 411', 411.

Figure 2B:
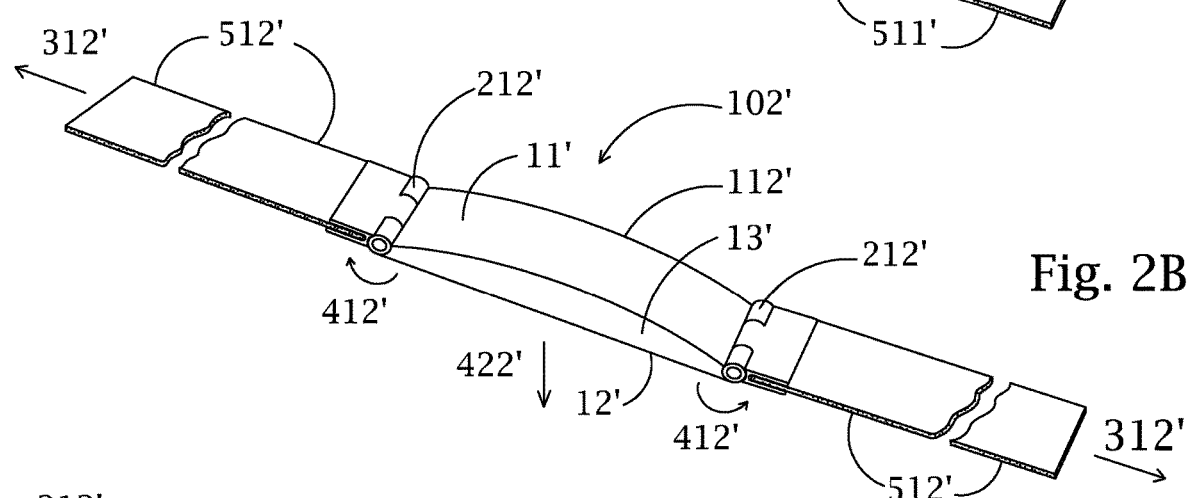
FIG. 2B is a side perspective view of a suture, built in accordance with a pin hinge embodiment of the present invention, with its spring in a fully stressed state and a partial sectional view of its surgical tape.
Figure 3B:
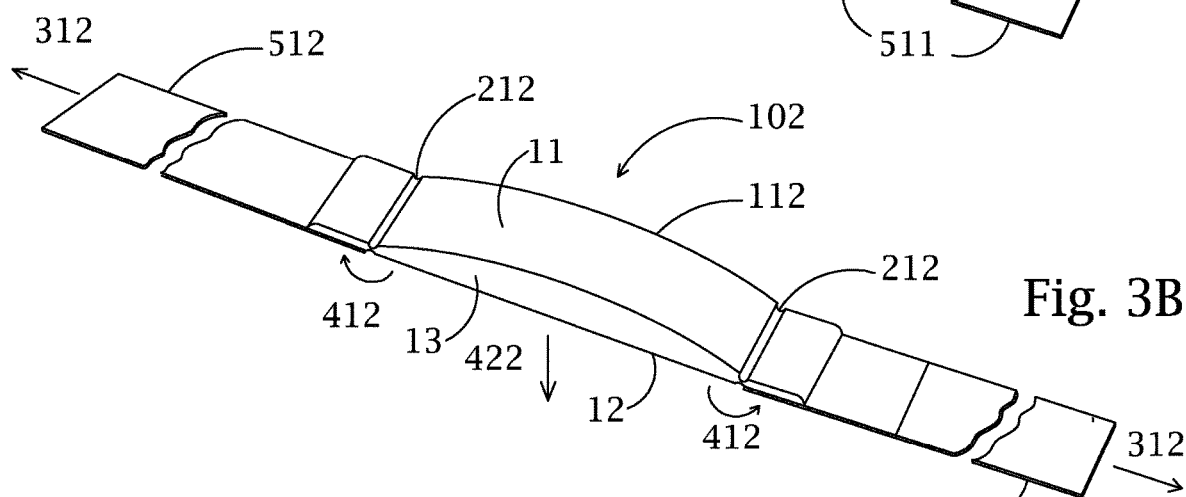
FIG. 3B is a side perspective view of a suture, built in accordance with a membrane hinge embodiment of the present invention, with its spring in a fully stressed state and a partial sectional view of its surgical tape.

Referring now to FIGS. 2B and 3B, the spring suture 102', 102 is shown in its fully stressed state of operation. To be placed in this fully stressed state, force in a stressing direction 312', 312 must be placed on the surgical tape 512', 512 on at least one side of the center spring 112', 112. Accordingly, it is contemplated that the spring suture 102', 102 can be placed in its fully stressed state by exerting force in the stressing direction 312', 312 on the surgical tape 512', 512 on one side of the center spring 112', 112 if the surgical tape 512', 512 on the other side is held in place or by exerting force in the stressing direction 312', 312 on the surgical tape 512', 512 on both sides of the center spring 112', 112 simultaneously.

When force in the stressing direction is placed on the surgical tape 512', 512 in such a manner, the center spring 112', 112 moves in a vertical flattening direction 422', 422, with the hinge members 212', 212 enabling the center spring 112', 112 to swing in a flattening direction 412', 412 relative to the surgical tape 512', 512 thereby flattening inner face 12', 12 and increasing a radius of the curve defined by outer surface 11', 11. The flattening of the center spring 112', 112 stores the mechanical energy employed and places it at a self-gauging level of pre-stress. Unlike prior art spring sutures, commonly embodied as either cylindrical, coil or leaf form, the center spring 112', 112 embodied as a convex-concave shaped spring having a variable thickness that progressively decreases from a center thereof to provide the spring with a bilateral, tapered cross-section. This shape provides the spring with a geometrical limit to the amount of pre-stress that may be applied thereto before the spring suture 102', 102 is placed on the incision or wound that is to be closed. This closure pre-stress is applied to the dermal level as partly described in the description of FIGS. 1A and 1B. It is contemplated that variation in the section detail of the spring, e.g., the radii of the curves defined by the respective inner and outer faces of the spring, and the specific mechanical qualities of the material of manufacture, elasticity, strength, etc., can offer different levels of closure pre-stress as may be suitable for different areas of the body, face, abdomen etc. In contrast, in prior art spring sutures, the correct amount of closure pre-stress is left unreferenced and solely to the skill of the applier.

Figure 2C:
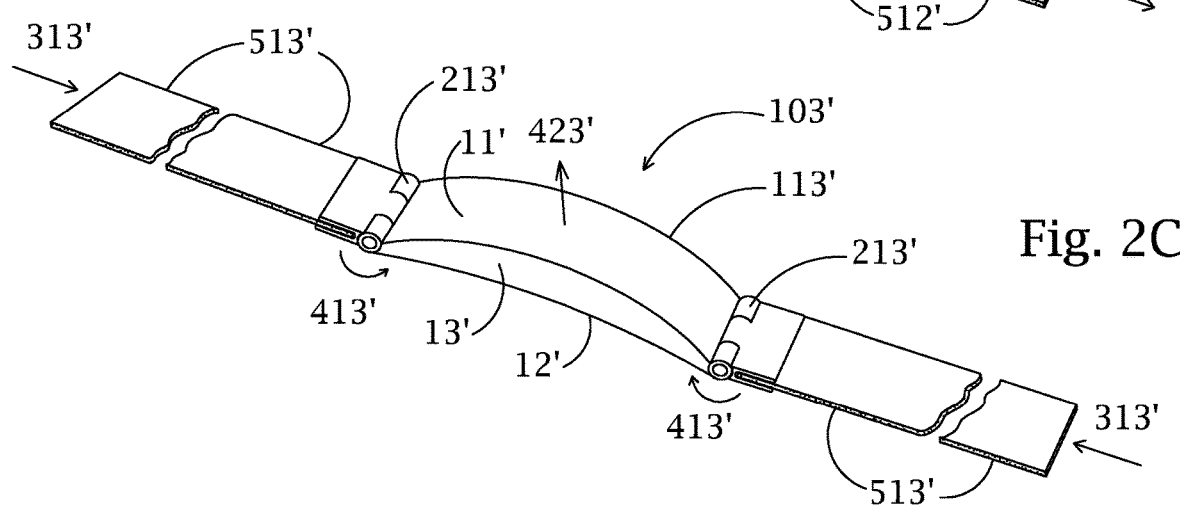
FIG. 2C is a side perspective view of a suture, built in accordance with a pin hinge embodiment of the present invention, with its spring in a retracted state and a partial sectional view of its surgical tape.
Figure 3C:
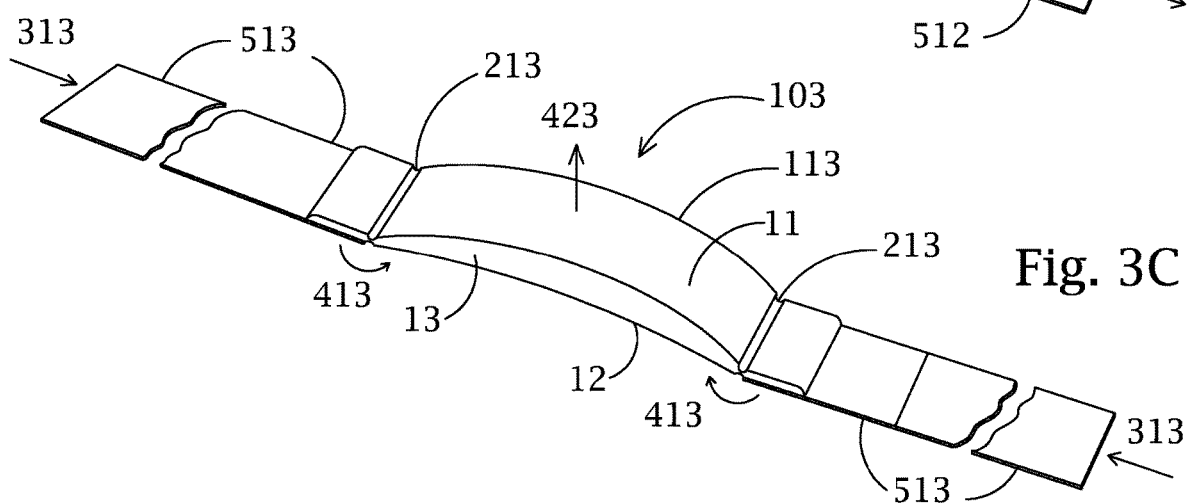
FIG. 3C is a side perspective view of a suture, built in accordance with a membrane hinge embodiment of the present invention, with its spring in a retracted state and a partial sectional view of its surgical tape.
Figure 4A:
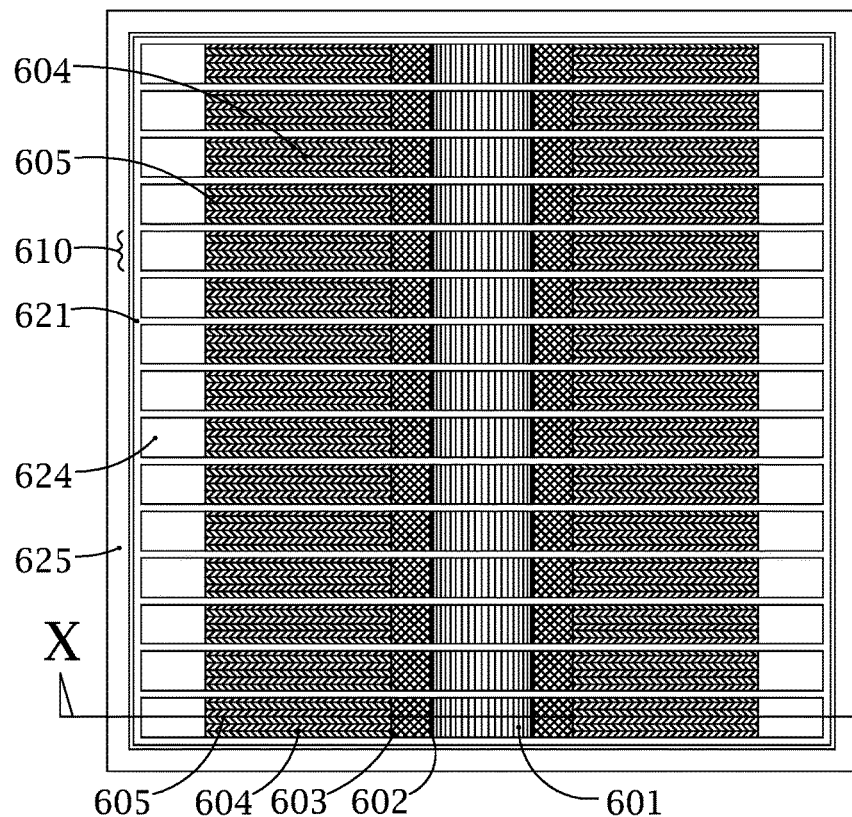
FIG. 4A is a top plan view of a plurality of sutures packaged side to side, in sterile packaging for commercial distribution.
Figure 4B:
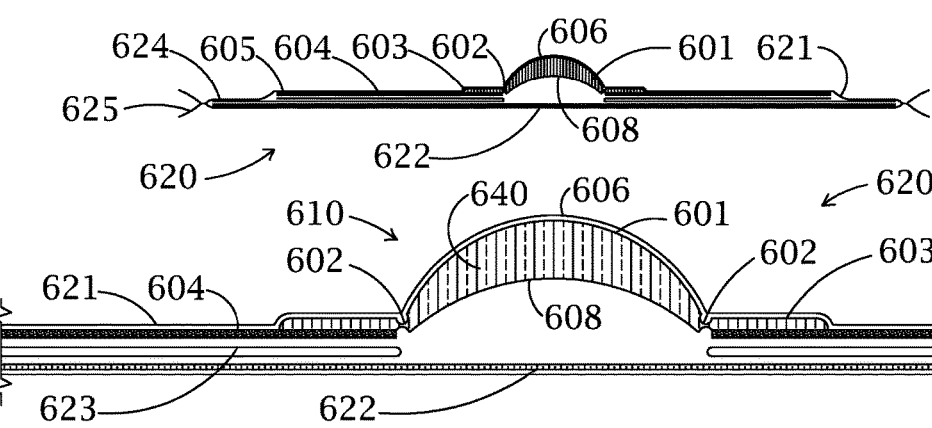
FIG. 4B is a side elevational view of a cross section of a suture built in accordance with a membrane hinge embodiment of the present invention, in sterile packaging for commercial distribution.
Figure 4C:
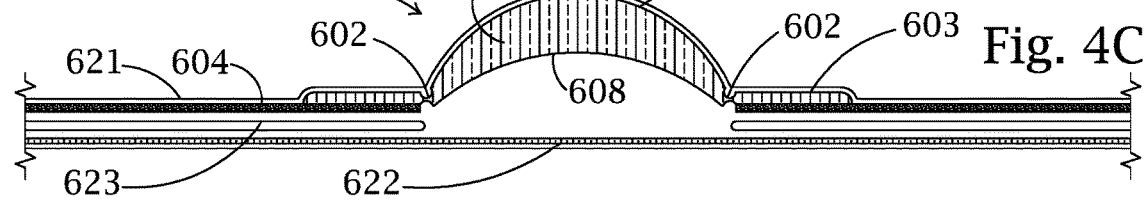
FIG. 4C is an enlarged, partial side elevational view of a cross section of the central section of suture built in accordance with a membrane hinge embodiment of the present invention, in sterile packaging for commercial distribution.
Figure 4D:
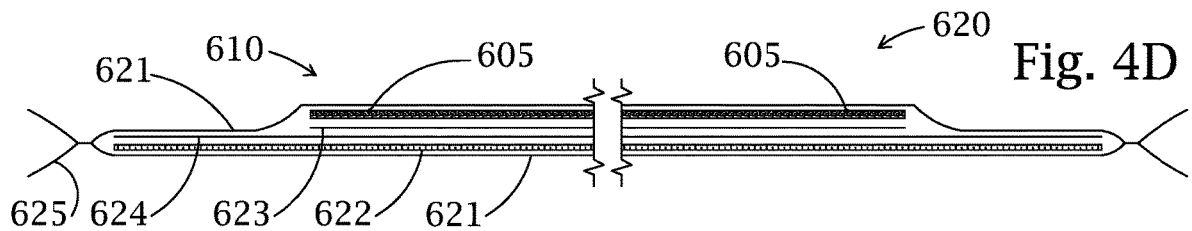
FIG. 4D is a side elevational view of a cross section of a suture built in accordance with a membrane hinge embodiment of the present invention with its end sections enlarged, in sterile packaging for commercial distribution.
Figure 5:
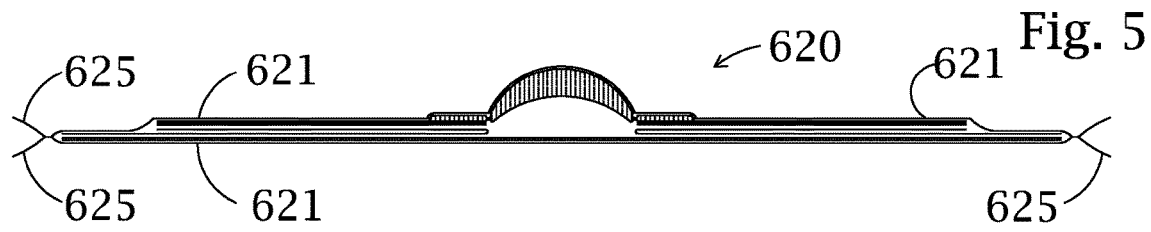
FIG. 5 is a side elevational view of a cross section of a suture built in accordance with a membrane hinge embodiment of the present invention, in sterile packaging for commercial distribution.
Figure 6:
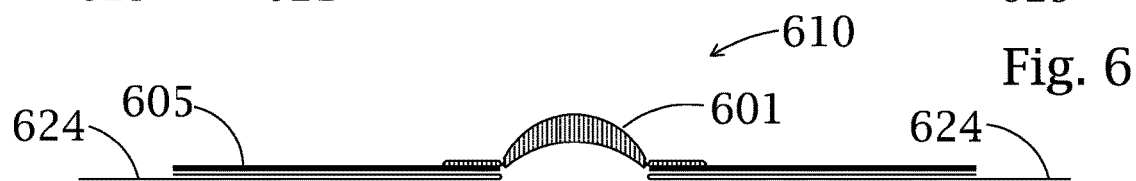
FIG. 6 is a side elevational view of a cross section of a suture built in accordance with a membrane hinge embodiment of the present invention and having been removed from its packaging.

Referring now to FIGS. 2C and 3C, the spring suture 103', 103 is shown in its retracted state of operation. In the retracted state, the center spring 113', 113 releases a portion of the mechanical energy stored when the spring suture 103', 103 was placed in a stressed state, exerting force in a horizontal retracting direction 313', 313 and motion in a vertical rising direction 423', 423 of the central spring 113', 113. The twisting motion 413', 413 is coincidental with the vertical rising direction of the spring 113', 113 is isolated from the retracting force 313', 313 and motion in the tape 513', 513 by the hinges 213', 213. The spring suture 103', 103 is constructed so that the surgical tape 513', 513 on both sides of the center spring 113', 113 can be attached to the skin of a wearer on either side of a targeted wound or incision. Thus, when force in horizontal retracting direction 313', 313 is applied by the center spring 113', 113, of a spring suture 103', 103 in place on a wearer, pre-stress is applied to the skin, remote from the wound or incision, so as to act through shear in the skin, down to the dermal level, to provide closure pre-stress at that level. More specifically, as the two sections of the surgical tape 513', 513 are drawn inward, in the closing direction 313', 313, by the force invested in the center spring 113', 113, the skin is drawn toward the wound or incision. The upper layer of skin acts through shear on the lower dermal layers so that they are also draw toward the incision from both sides. This causes compression at the dermal level, at the line of the incision. In order to let this compression act to result in abutment of the lower layers of the skin, relief space is provided for the swelled volume of the compressed upper layers of skin, under the spring, as the central part of the spring rises simultaneously, as it retracts.

It understood that the hinge members 213', 213 enable the spring suture 103', 103 to isolate the flexure forces in the center spring 113', 113 from the surgical tape 513', 513 while in use on a wearer. Such isolation prevents the twisting forces of the center spring 113', 113 from being applied to the skin around the wound or incision, thereby preventing distortion and misalignment of the skin which is detrimental to healing.

Referring now to FIGS. 4A, 4B, 4C, 4D, 5, 6, and 8A, the spring suture 610 is shown in various states of the preferred commercial packaging and deployment therefrom. The spring suture 610 is typically distributed as a sterile package 620, containing a plurality of discrete spring sutures 610 packaged side by side. The sterile package 620 typically includes a sterility wrapper 621 that includes a peeling edge 625 and a packing card 622. A doubled back tape release strip 623 having a free end 624 is additionally included to improve the ease of application of the spring sutures 610 at the incision.

Each discrete spring suture 610 includes a center spring 601, a membrane hinge 602 and a welding flange 603, all of which are nominally nylon or similar polymer, extruded together as one. Center spring 601 includes an outer convex face 606, an opposing concave inner face 608 and a variable thickness 640 extending to and between the outer face and the inner face. The variable thickness of spring 610 is greatest at the center of the spring and progressively decreases moving laterally therefrom so that spring 601 exhibits a bilateral, tapered cross-section. Connection is made between the center elements, the spring 601, the hinge 602 and the welding flange 603, and the surgical tape 604, at the welding flange 603. The bond is made by thermal weld between the nylon extrusion and the conventional surgical tape normally made of spun bonded nylon. The doubled back tape release strip 623 is included with the surgical tape 604 when the tape and the center are connected.

While the surgical tape 604 generally exerts force from the center spring 601 on the skin of a wearer, it is understood that because it stretches less easily than skin, the surgical tape's distal end 605 primarily supplies the transfer closure force from the spring suture 610 structure to the surface of the skin, remotely from the edges of the wound or incision at the distal end 605.

Figure 7A:
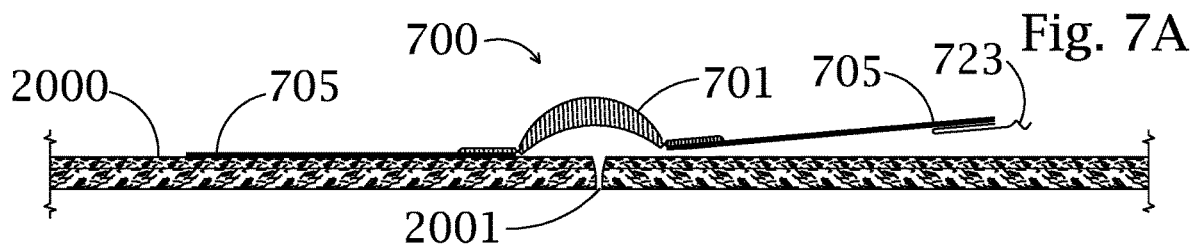
FIG. 7A is a side elevational view of a cross section of a suture, built in accordance with a membrane hinge embodiment of the present invention, in a non-stressed state and with one end section attached to a wearer.

Referring now to FIG. 7A, the spring suture 700 is shown being placed over an incision 2001 on the skin 2000 of a wearer. The spring suture 700 has the tape release strip 723 removed (not shown) on the surgical tape 705 on the left side of the center spring 701, with the surgical tape 705 on the left side of the center spring 701 applied to the skin 2000 of a wearer, affixing it thereto. The spring suture 700 is positioned on the wearer so that the center spring 701 is disposed over the target incision 2001. On the right side the tape release strip 723 has been partly removed to partly expose the adhesive on the underside of the surgical tape 705, but remains at the end to enable the distal end of the surgical tape 705 to be grasped for stretching. As the spring suture 700 is shown prior to being stretched, the center spring 701 is shown in its resting convex-concave form.

Figure 7B:
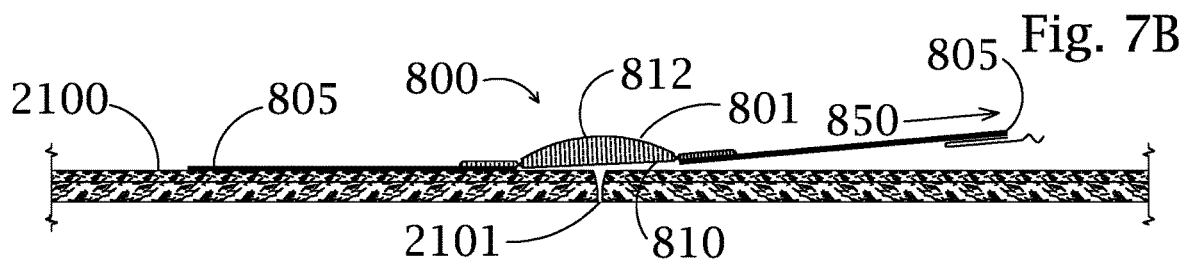
FIG. 7B is a side elevational view of a cross section of a suture, built in accordance with a membrane hinge embodiment of the present invention, with one end section attached to a wearer and with a pre-stressed spring.

Referring now to FIG. 7B, the spring suture 800 is shown being stretched over an incision 2101 on the skin 2100 of a wearer with an inner surface 810 of center spring 801 facing the skin 2100 of the wearer and an outer surface 812. The surgical tape 805 on the left side of the center spring 801 affixed to the skin 2100 of a wearer, and force in a stretching (or stressing) direction 850 is being placed on the surgical tape 805 on the right side of the center spring 801. The application of the force in a stretching direction 850 is required to pre-stress the center spring 801, in preparation for the of the application of the surgical tape 805 on the right side of the spring suture 800 to the skin 2100 on the right side of the incision 2101. As this occurs, inner face 810 of spring 801 is essentially flattened and a radius of the curve defined by outer face 812 is gradually increased.

Figure 7C:
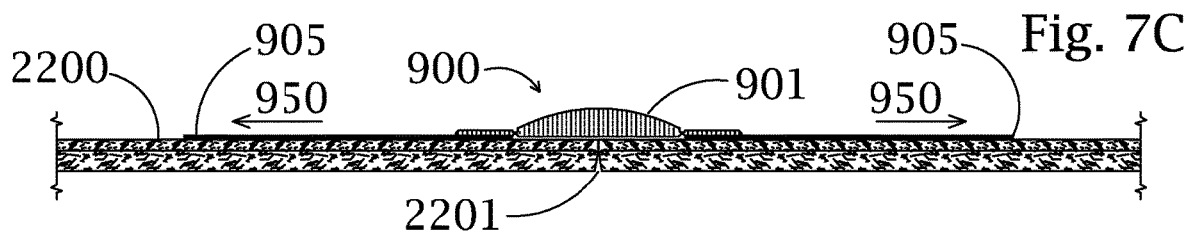
FIG. 7C is a side elevational view of a cross section of a suture, built in accordance with a membrane hinge embodiment of the present invention, with both end sections attached to a wearer and with a pre-stressed spring.

Referring now to FIGS. 7C and 8B, the spring suture 900 is shown with both sides of the surgical tape 905 applied to the skin 2200 on either side of the incision 2201. The pre-stress is maintained in the center spring 901, following the application of the second side of the surgical tape 905 to the skin 2200, by the stretching force 950, maintained prior to the release of the tape 905, by the applier. The incision 2201 is shown closed at the top as the edges thereof have been manually drawn tightly together, by the applier, at the epidermal level.

Figure 7D:
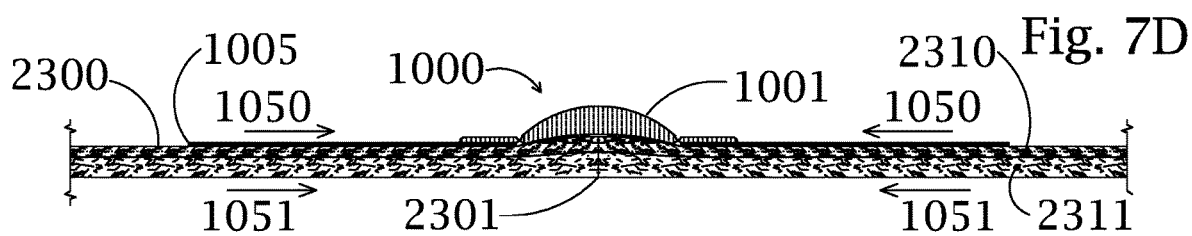
FIG. 7D is a side elevational view of a cross section of a suture, built in accordance with a membrane hinge embodiment of the present invention, in a retracted state and with both end sections attached to a wearer.

Referring now to FIGS. 7D and 8C, the spring suture 1000 is shown retracted in place on the skin 2300 of a wearer, over a target incision 2301 with outer face 812 defining a radius that is greater than the radius defined by outer face when in the non-stressed state and less than the radius defined by the outer face when in the stressed state. Following the initial application of the spring suture 1000, as shown in FIGS. 7C and 8B, the release of the stored force in the center spring 1001 from the manual stretching causes the spring suture 1000 to take its retracted position. In the retracted position, the center spring 1001 exerts force in a retracting (or closing) direction 1050. This force is transferred to the epidermal level of the skin 2310, by the distal ends of the spring suture 1000 through the attachment of the surgical tape 1005 to the skin 2300, with the distal ends at a location remote from the incision 2301. This force in a retracting direction 1050 on the epidermal level of the skin 2310, acts through shear in the skin down to the dermal level 2311, to provide dermal closure force 1051, through skin compression, resulting in abutment at the line of the incision 2301. The incision 2301 is shown closed at the dermal level 2311 of the skin 2300. During this process, the compressed tissue around the incision 2301 rises into the recess that develops under the center spring as it retracts, rising as it tends to return to its original convex-concave form.

It is contemplated that the application of closure pre-stress to the skin, remote from the line of the wound or incision, then acting through shear in the skin to provide dermal level compression closure force in conjunction with providing a relief space for the compressed tissue enables the spring suture to overcome the classical problem of skin inversion common to prior art skin tapes, while maintaining the advantage over staples or stitches, of being non-invasive, that is also common to prior art skin tapes.

Referring now to FIGS. 8A, 8B, and 8C, it is recognized that the horizontal span of the spring suture 600, 900, 1000 varies depending on whether the spring suture is in a non-stressed state 600, a stressed state 900 or a retracted state 1000. A non-stressed state spring suture 600, defined by its un-stressed central spring 601, will have the smallest horizontal span.

A fully stressed state spring suture 900, defined by a center spring 901 under the effect of the applied stretching direction 950, has the largest horizontal span. It is appreciated that the flattening of the center spring 901 acts as an inherent limit to the stretch of the center spring 901, making the self-gauging property of the center spring 901 possible. This self-gauging action enables the automatic provision of the correct, designed level of closure force, for any particular application of any particular version of spring suture.

A retracted state spring suture 1000, defined by the center spring 1001 in an intermediate position between unstressed and stressed and exerting force in a retracting direction 1050 on attached surgical tape 1005, has a horizontal span between that of the non-stressed spring suture 600 and a stressed spring suture 900. The application of the force in a retracting direction 1050 at the surface of the skin 2300 through the surgical tape 1005 is transferred through shear to become dermal closure force 1051 at the base of the skin, against the underlying tissue (not shown). The dermal closure force 1051 at the dermal level provides the compression force that allows dermal level closure. The self-gauging aspect of the spring geometry allows for the magnitude of the closure force to be designed to be correct for the specific application on a structural level, through selection of i.e. cross section geometry and elastic modulus of material.

The independence of the linear closure forces 1050, 1051 acting on the skin 2300, from the twisting flexural forces in the center spring 1001, is ensured through the hinge members 1011 disposed on opposite sides of the center spring 1001, respectively. The independence of the forces allowed by the hinge members 1011, in conjunction with the designable, self-gauging level of closure force, provide for wound or incision closure of the highest accuracy. This in turn provides for minimum blood clotting volume, therefore minimum scarring and most rapid healing.

Referring now to FIG. 9, a plurality of spring sutures 1101 are shown attached to the surface of a wearer's skin 1100 in an arc pattern as might be the case in an actual application. The spring sutures 1101 are shown spaced for easy application to the skin 1100 but close enough together so that when acting remotely from the incision line provide essentially continuous closure force 1150 across the incision line 1102 to provide completed closure as shown. A polymerizing skin adhesive 1110 may be applied to the distal ends of the spring sutures 1101, typically on the surgical tape thereof, once the accuracy of the final closure has been confirmed. Acrylates that are compatible with skin 1100 are contemplated for this purpose, to provide maximum security of the closure. The structure of the spring sutures 1101, particularly the lack of any adhesive on the actual incision, make it appropriate for use with an anti-biotic ointment 1111 to keep the wound clean and free from infection as well as to keep it from scabbing so as to minimize superficial scarring and discomfort, following the primary closure of surgical incisions. It is contemplated that such an ointment 1111 may be applied over and between the sutures and may occupy a slender interstitial space between the base of the center spring and the top of the enclosed skin.

The present invention has been shown and described herein in what is considered to be the most practical and preferred embodiment. It is recognized, however, that departures may be made therefrom within the scope of the invention and that obvious modifications will occur to a person skilled in the art.

What is claimed is:
1. A suture comprising:
  an elongate resilient spring member including a solid body having a first end, a second end, an outer face, an inner face opposing the outer face, a variable thickness extending to and between the inner face and the outer face and a bilateral, tapered cross-section,
  a first attachment strip coupled to the first end, the first attachment strip being configured for adhering to a wearer,
  a second attachment strip coupled to the second end, the second attachment strip being configured for adhering to a wearer,
  a non-stressed state, and
  a stressed state, wherein the spring member includes a midsection and the variable thickness progressively decreases moving bilaterally from the midsection to the first end and the second end, respectively, and wherein, when the elongate resilient spring member is the non-stressed state, the inner face is concave-shaped, the elongate resilient spring member includes the bilateral, tapered cross-section and the outer face is convex-shaped, and when the elongate resilient spring member is in the stressed state, the inner face is essentially flat and the outer face is convex-shaped.

2. The suture of claim 1 the first attachment strip is connected to the spring member through an attachment member and a hinge member disposed on the first end.

3. The suture of claim 2 wherein a membrane hinge defines the hinge member.

4. The suture of claim 3 wherein a welding flange defines the attachment member.

5. The suture of claim 4 wherein the welding flange, the hinge member and the spring member comprise a single, continuous extrusion.

6. The suture of claim 1 wherein surgical tape defines at least one of the first attachment strip and the second attachment strip.

7. The suture of claim 1 wherein at least one of the first attachment strip and the second attachment strip includes an adhesive.

8. The suture of claim 1, wherein the solid body extends to and between the first end and the second end and to and between the convex outer face and the inner face opposing.

9. A suture comprising:
a spring member including a first end portion, a second end portion, a length extending between the first end portion and the second end portion and having a midsection, an outer face, an inner face opposing the outer face, a material having a thickness extending to and between the convex outer surface and the inner surface that progressively decreases moving laterally from the midsection towards the first end portion and the second end portion, respectively,
a first attachment strip coupled to the first end portion,
a second attachment strip coupled to the second end portion, and
wherein, when the spring member is a non-stressed state, the inner face is concave-shaped, the spring member includes a tapered cross-section and the outer face is convex-shaped, and when the spring member is in a stressed state, the inner face is essentially flat and the outer face is convex-shaped.

10. The suture of claim 9 wherein the spring member exhibits a bilateral, tapered cross-section.

11. The suture of claim 10 wherein, when the suture is in the stressed state, the bilateral, tapered cross-section is defined by the convex outer face and the inner face, the inner face being essentially flat.

12. A suture comprising:
an elongate resilient member including a solid body, a first end portion, a second end portion opposing the first end portion, a midsection, an outer face configured to face away from a wearer, an inner face configured to face towards the wearer, a variable thickness extending to and between the inner face and the outer face that progressively decreases moving laterally from the midsection towards the first end portion and the second end portion, respectively, and a tapered cross-section,
a first attachment strip coupled to the first end portion, and
a second attachment strip coupled to the second end portion,
wherein, when the resilient member is a non-stressed state, the inner face is concave-shaped, the resilient member includes the tapered cross-section and the outer face is convex-shaped, and when the resilient member is in a stressed state, the inner face is essentially flat and the outer face is convex-shaped.

13. The suture according to claim 12, wherein the variable thickness extends through the solid body.

* * * * *